(12) United States Patent
Mosbaugh

(10) Patent No.: US 6,489,047 B2
(45) Date of Patent: Dec. 3, 2002

(54) METHOD OF SHAPING POROUS AGGLOMERATIONS OF FUSED MICROSPHERES

(75) Inventor: Jim Mosbaugh, Tampa, FL (US)

(73) Assignee: Tatho Materials, Inc., Tampa, FL (US)

( * ) Notice: Subject to any disclaimer, the term of this patent is extended or adjusted under 35 U.S.C. 154(b) by 67 days.

(21) Appl. No.: 09/792,720

(22) Filed: Feb. 23, 2001

(65) Prior Publication Data

US 2002/0036364 A1 Mar. 28, 2002

Related U.S. Application Data

(60) Provisional application No. 60/184,816, filed on Feb. 25, 2000.

(51) Int. Cl.$^7$ ................................................ A61K 7/46
(52) U.S. Cl. ........................... 428/905; 512/1; 264/117; 264/119; 264/128; 63/DIG. 2
(58) Field of Search ................................ 264/117, 119, 264/128; 428/905; 63/DIG. 2; 512/1

(56) References Cited

U.S. PATENT DOCUMENTS 6,245,733 B1 * 6/2001 Mosbaugh ................... 428/905

* cited by examiner

*Primary Examiner*—Jill Warden
*Assistant Examiner*—Monique T. Cole
(74) *Attorney, Agent, or Firm*—Fowler White Boggs Banker, P.A.; Dennis L. Cook, Esq.; James M. Matulis, Esq.

(57) ABSTRACT

A method for molding an agglomeration of fused microspheres to create a fragrance delivery system by use of room temperature setting binders. The molded pre-glass agglomeration has an extended fragrance release time exceeding a year and a half, and uses microcapillary action to quickly uptake oils and alcohols. The molded pre-glass agglomeration provides a slow release of fragrance without the escape of any residual liquid. The molded pre-glass agglomeration may be replenished, an unlimited number of times, with fragrance containing oils and alcohols after the odor fades. The molded pre-glass agglomerations may also be colored or dyed.

24 Claims, 2 Drawing Sheets

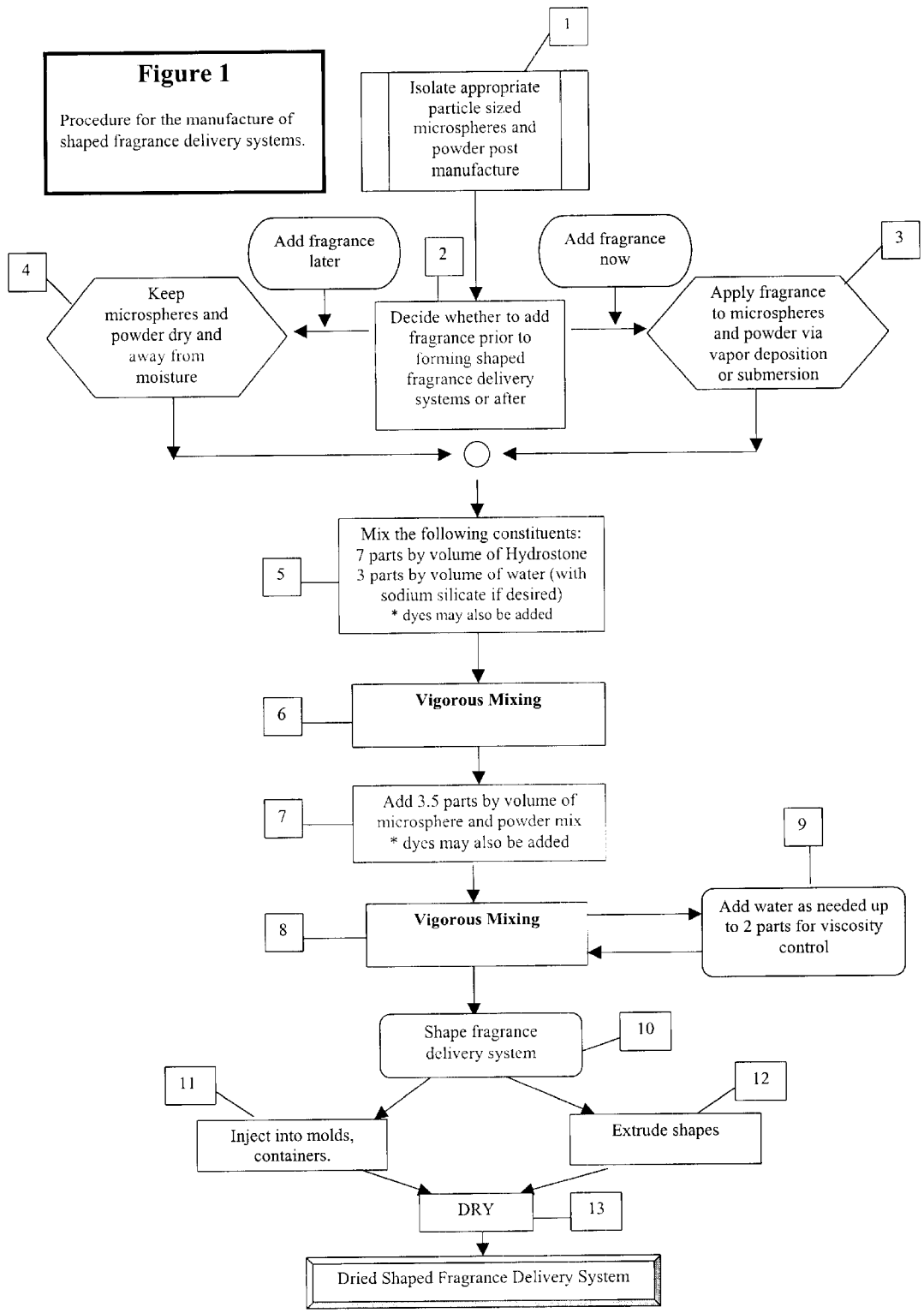

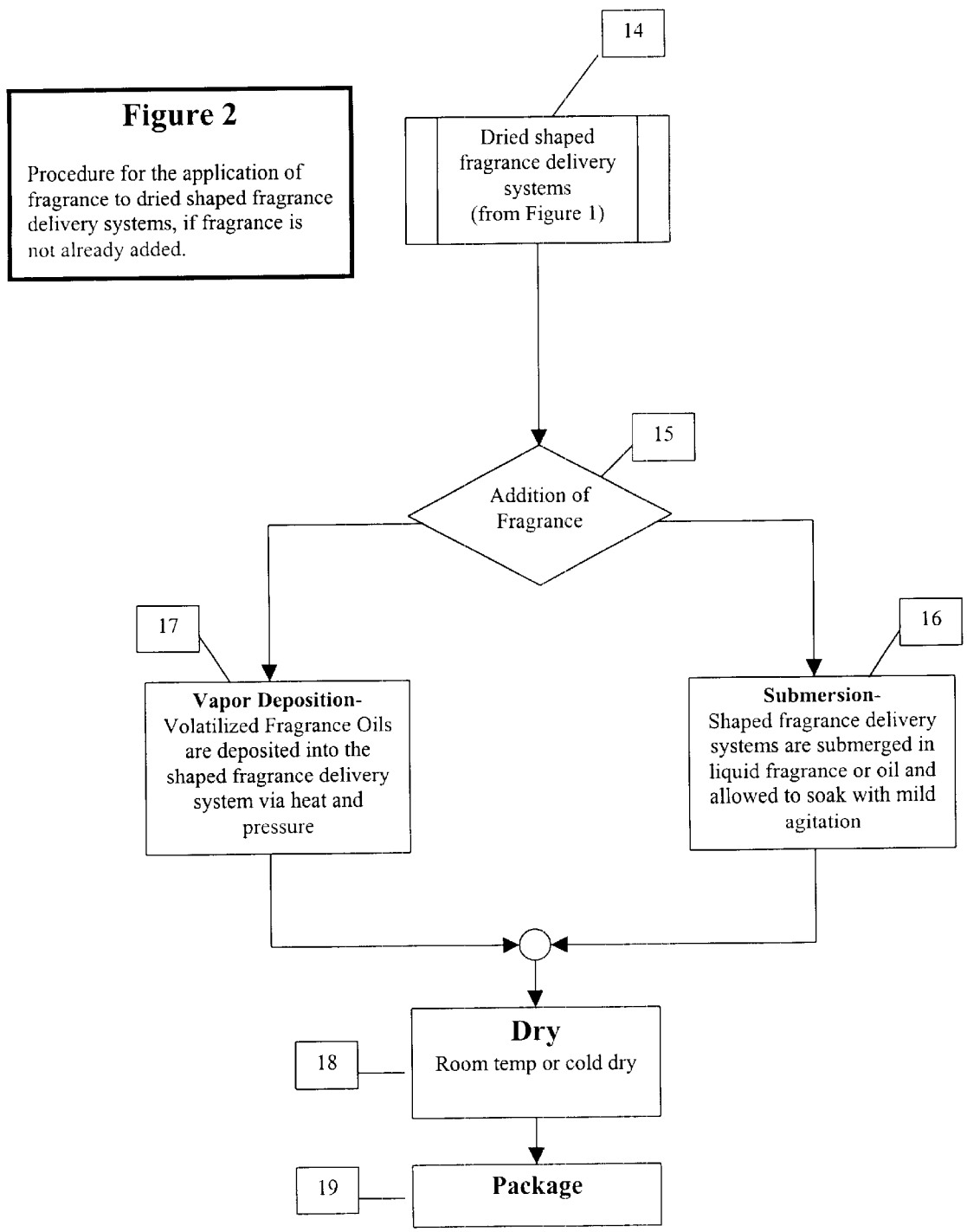

METHOD OF SHAPING POROUS AGGLOMERATIONS OF FUSED MICROSPHERES

CROSS-REFERENCE TO RELATED APPLICATION

The present application claims the benefit of previously filed co-pending Provisional Patent Application, Ser. No. 60/184,816 filed Feb. 25, 2000, and incorporates the contents by reference.

FIELD OF THE INVENTION

The present invention relates to fragrance delivery systems and a method for making the same. In particular, the invention relates to a method of making a fused agglomeration of microspheres by using modifiers and silicates, and for molding that agglomeration into a shaped fragrance delivery system by use of room temperature setting binders. The agglomeration of fused microspheres may be used to adsorb fragrance-producing oils and volatiles, and then release the fragrance innate to the oils and volatiles over an extended period of time without being messy or wet.

BACKGROUND OF THE INVENTION

Most delivery systems that utilize microspheres are manufactured out of acrylates or non-siliceous polymers. There are no fragrance delivery systems that utilize soda lime borosilicate microspheres fused together naturally without additives. Most fragrance systems have a short life span and lose their aroma within a few months. Virtually no currently available fragrance systems last for longer than a few months under any circumstances. Most also have a very intense smell initially with a reasonably pleasant odor after a few weeks which fades fairly fast.

Microspheres have been used in the past for a variety of purposes. The most common uses pertain to holders for chemicals in compositions such as holding fragrance for laundry detergent. In other words, the microspheres contain a chemical and are mixed with other compounds to form a heterogeneous composition where the microspheres will release the chemicals either gradually or all at once in response to a stimulus such as a change in ionic character, heat or other stimulus. Microspheres are also used in drug delivery systems designed to release the drug contained in the microspheres at a particular time according to pH or other factors.

The material and use of the pre-glass agglomeration of this invention are unique and unknown in the past. The pre-glass agglomeration discussed in this present invention has been disclosed by the inventor of this application, James Mosbaugh, in U.S. patent application Ser. No. 09/302,270, filed on Apr. 30, 1999, and the text and disclosure contained in that application is hereby referenced and contained herein. U.S. patent application Ser. No. 09/302,270 has now been allowed, but has not yet issued.

The pre-glass agglomerations disclosed in the present invention are not discrete spheres but rather modified soda-lime borosilicate sphere clusters, wherein thousands of microspheres become molecularly fused together via microcrystalline-like structures on the sphere surfaces. Therefore, this invention starts with the creation of a micro sphere matrix that is then molded into aesthetically pleasing or useful shapes with the addition of room temperature setting binders, thus creating a shaped fragrance delivery system. Fragrant liquids or oils may then be added. The shaped fragrance delivery system is also referred to herein as an artificial rock fragrance delivery system, because prior to molding, the pre-glass agglomeration resembles a rock or rock-like structure. These shaped microcrystalline structures are distinctly different from currently available industrially manufactured microspheres.

U.S. Pat. No. 3,365,315 issued to Beck et al. on Jan. 23, 1968 discloses glass bubbles made from glass cutlet particles by heating. This amorphous solid contains $SiO_2$ (60–80%), $Na_2O$ (5–26%), $CaO$ (5–25%), $K_2O/Li_2O$ (5–16%), and $Na_2O/K_2O/Li_2O$ (5–16%) plus some other oxides. The temperature range utilized for bubble formation is between 1050°C. and 1300°C. The resultant amorphous solid can be utilized as ingredients in molded parts designed for use in high pressure environments. These particles also have the capacity to be used with thin walls thus possessing a maximum strength, yet crushable if that strength is exceeded. The methods utilized to make the glass bubbles taught by Beck, as well as the glass bubbles themselves, are very different from the rock of the present invention.

U.S. Pat. No. 3,985,298 issued to Nichols on Oct. 12, 1976 discusses controlled release materials, and method of using, which can be incorporated into a chemical delivery system. The materials utilized by Nichols are polymer-liquid composite materials that may contain 99% or more of the liquid. These controlled release materials can be incorporated into aerosol propellants, food products, chewing gum, pharmaceutical compounds, agricultural products, or cosmetic preparations. The desired functions of the release materials are flavoring, scent, coloring, medication, dermatological action, pesticidal action, or agricultural fertilizer. The materials and objectives utilized by Nichols are different from the present invention.

U.S. Pat. No. 4,155,897 issued to Schlusener on May 22, 1979, discloses compositions exhibiting controlled release of an active substance. The compositions of Schlusener comprise an unsaturated polyester resin, an active substance, hollow microspheres of an organic material, and an inorganic material. The hollow microspheres can be made of glass and are mixed with an unsaturated polyester resin to make a molded solid or semisolid substance. An active ingredient, such as volatile oils, is added to the substance. The strength of the final product depends on the unsaturated polyesters used, but is less than the strength of the unsaturated polyester used because the hollow microspheres reduce the overall strength. The composition taught by Schlusener is different from the amorphous rock of the present invention. The release of gas by the Schlusener composition is measured by a period of up to about half a year which is significantly less than the year and a half capacity of the present invention. The Schlusener composition results in a relatively high gas release rate the first week, less the next three weeks and even less for the remainder of the active time. Also, the compositions of Schlusener lack the strength and low density combination of the present invention.

U.S. Pat. No. 5,336,665 issued to Garner-Gray et al. on Aug. 9, 1994, discloses a hydrophobic porous inorganic carrier particle having a perfume absorbed into the particle. In particular, a detergent composition containing the carrier particle and a method for manufacturing the same is disclosed. The inorganic carriers used in Garner-Gray include aluminosilicates such as certain zeolites, clays, aluminas and silicas, all of which are chemically treated or naturally hydrophobic. These porous, inorganic carrier particles are not designed to release odor over an extended period of time, but to deliver perfume to clothing or other surfaces via a detergent or the like. The particles used in Garner-Gray are not designed for room deodorizers, are not strong, and are not exceptionally adsorbent in that they are hydrophobic and would not adsorb water or alcohols.

U.S. Pat. No. 5,725,869 issued to Lo on Mar. 10, 1998, describes microsphere reservoirs for controlled release applications. The microspheres, optionally containing an ingredient to be dispensed through controlled release, are prepared by solvent evaporation of an oil-in-water emulsion formed from an organic solvent containing a polymer and a plasticizer, and an aqueous solution containing one or more emulsifying agents. The microcapsules formed are porous and spongy in structure as opposed to hollow. These microspheres have a relatively high load rate and a low dispersion rate. They are useful for agricultural chemicals, pharmaceuticals, cosmetics and fragrances. The invention of Lo is not designed to be a room deodorizer, and does not have a sturdy solid nature as does the molded rock of the current invention.

U.S. Pat. No. 5,824,345 issued to Milstein on Oct. 20, 1998, discloses a method for preparing compositions which are useful in the delivery of fragrances and flavorants. The active agent is mixed with the proteinoid or a hydrolyzed vegetable protein solution. The proteinoid or modified hydrolyzed vegetable protein is precipitated out of the solution, thereby forming a microsphere containing the active agent. Milstein differs from the present invention in that the present invention adsorbs any liquid, oil or alcohol, while Milstein requires the microspheres to be made concurrent with placing the agent therein, a handicap that it reduces the usefulness of the Milstein invention. Also, the microsphere of Milstein is not as sturdy as the current invention and the aroma does not last nearly as long.

U.S. Pat. No. 5,849,055 issued to Arai et al. on Dec. 15, 1998, discloses a process for making inorganic microspheres which comprises pulverizing a material by wet pulverization to obtain a slurry of a pulverized powder material, spraying the slurry to form liquid droplets, and heating the liquid droplets to fuse or sinter the powder material to obtain inorganic microspheres. These microspheres are discrete individual microbeads and cannot be utilized in the manner of the present invention. The microspheres of Arai can be used as a powder or an ingredient, but not as a deodorizing molded rock.

U.S. Pat. No. 5,871,722 issued to Nacht et al. on Feb. 16, 1999, discloses ionic beads useful for controlled release and adsorption. Active ingredients are released from the ionic polymer beads over an extended period of time such as when orally administered, or when applied to a keratinic material, typically human skin or hair, or when otherwise delivered to a target environment. Clearly, the ionic beads of Nacht are designed to deliver an active ingredient upon contact with some substance which releases their ionic bonds. These ionic beads would not be useful for room deodorants or absorption of oils.

U.S. Pat. No. 5,534,348 issued to Miller et al. on Jul. 9, 1996, describes hollow borosilicate microspheres and a method of making them. The compositions of the sodium borosilicate starts with the preferred weight ratio of $Na_2O:SiO_2:B_2O_3$ between 1.0:2.5:0.2 and 1.0:3.22:0.5 for the starting material. The borosilicate microspheres of Miller are used in reflective paints and coatings, incorporated into molded plastic products, and for use as thermal insulation, but not as delivery vehicles for scents or as adsorbent materials.

There are no known methods of shaping fragrance delivery systems that use calcined gypsum cement or similar materials as binding agents of microspheres. Rather, calcined gypsum is more commonly used as a building material. There are also no known binders for use with shaped fragrance delivery systems utilizing microspheres which are effective at room temperature. None of the above inventions and patents, taken either singularly or in combination, is seen to describe the instant invention as claimed. Thus, a shaped artificial rock fragrance delivery system solving the aforementioned problems is desired.

SUMMARY OF THE INVENTION

The current invention relates to an agglomeration of fused microspheres that acts as a vector for fragrance delivery by utilizing fused microspheres with calcium integrated into the spheres from an aqueous sol precursor, where that agglomeration of fused microspheres is then molded into aesthetically pleasing shapes by use of room temperature setting binders. The fragrance delivery system has an extended fragrance release time generally exceeding a year and a half. The pre-glass agglomeration of fused microspheres uses microcapillary action to quickly uptake oils and alcohols to more than double the weight of the pre-glass agglomeration. Also, the slow release of fragrance without any residual liquid escape is another advantageous quality of the instant pre-glass agglomeration invention. It is also possible to recharge or replenish the shaped fragrance delivery systems of the present invention an unlimited number of times with additional fragrance oils or alcohols after the odor fades.

The shaped fragrance delivery systems can be used for aromatherapy crock pots or boilers, as room or facility fragrances to counteract pungent odors, and as insect repellent delivery systems by soaking the molded agglomeration in citronella, lavender or other repellant. The fragrance delivery systems may be colored or dyed as desired. Those skilled in the art will recognize other uses of a material with those qualities of the present invention.

Accordingly, it is a principal object of the invention to provide a shaped fragrance delivery system that has exceptional adsorption qualities, and is dry to the touch once removed from the substance to be adsorbed and allowed to dry. It is another object of the invention to provide a molded agglomeration of fused microspheres that can adsorb substances and then slowly release those substances over time. It is another object of the invention to provide a molded agglomeration of fused microspheres that can adsorb oils and other lipophilic substances readily without significant mess. It is a further object of the invention to provide a molded agglomeration of fused microspheres that can adsorb alcohol-based liquids readily. Still another object of the invention is to provide a molded agglomeration of pre-glass material that, after adsorption of an aromatic oil or alcohol-based substance, will release the fragrance of the adsorbed substance over an extended period of time. It is an object of the invention to provide improved elements and arrangements thereof for the purposes described which is inexpensive, dependable and fully effective in accomplishing its intended purposes. These and other objects of the present invention will become readily apparent upon further review of the following Specification.

BRIEF DESCRIPTION OF THE DRAWINGS

These and other advantages of the invention may be more clearly understood with reference to the Specification and the drawings, in which:

FIG. 1 is a diagram of a preferred methodology for the manufacture of shaped fragrance delivery systems;

FIG. 2 is a diagram of an alternative methodology for the application of fragrance to dried shaped fragrance delivery systems.

DETAILED DESCRIPTION OF THE INVENTION

The present invention pertains to shaped fragrance delivery systems that comprise highly adsorbent pre-glass agglomerations which can be shaped by use of room temperature binders. Specifically, the present invention relates to a system that acts as a vector for fragrance delivery made up of fused microspheres with calcium integrated into the spheres from an aqueous sol precursor. According to the present invention, the fused microspheres may be molded into shapes by use of room temperature setting binders. The pre-glass agglomeration can be utilized in diverse ways. It can be used to adsorb oil-based or alcohol-based liquids. Upon absorption of liquids, the surface of the pre-glass agglomeration is dry to the touch, thus eliminating any potential mess or stickiness. The pre-glass agglomeration is a fragrance delivery system that will release the fragrance of oil-based or alcohol-based aromatic liquids slowly over a sustained period of time, generally up to about one and a half years.

Example 1 will disclose how the fused microspheres may be manufactured. Example 2 discloses how these fused microspheres will then be bound together by use of room temperature setting binders, and then fashioned into a shaped fragrance delivery system. Example 3 will then describe a method for preparing a small-scale batch of shaped fragrance delivery systems.

EXAMPLE 1

Manufacture of Microspheres

First the pre-glass agglomeration adsorptive material is made. Preferably, commercial silicates are utilized such as sodium silicate having a weight ratio 3.22, or sodium silicate modified with a caustic agent or acetate having a weight range between 2.8–3 silicate to alkali, or potassium silicates such as KASIL (PQ Corporation) having a weight ratio 2.44 are used. Modifiers such as technical grade boric acid and calcium nitrate are also used. The slurry for the modifiers is approximately 8–18% solids. The total solution is between 20–40% solids. Other modifiers may be added in quantities from about 1–10%. These other modifiers may include Pb, MgO, $Al_2O_3$, BaO, $Li_2O$, Ge, and S.

A preferred method of making the pre-glass agglomeration comprises the following steps: The constituents are mixed together in two separate factions comprising the silicate part and the modifier part. The modifier part is boric and calcium in an aqueous slurry. The modifier solution is either poured into the silicate solution with vigorous mixing or the two are mixed together using an impeller pump with a recirculation loop. Vigorous mixing and slow addition of the boric/calcium solution are essential.

The solution, once mixed together, has a pH of 10–12. Mixing temperatures approach 60° C. This solution is spray dried using a two-fluid nozzle, or alternatively, a centrifugal atomizer operated at 10,000–25,000 rpm. While air atomizing, air pressure varies between 80-1000 psi. The outlet temperature is 300–800° F.

The spray-dried product is then fed via pneumatic conveyor to a rotary tube furnace. The powder is fed into the furnace via an Accurate Feeder to a 316 SS tube rotating at 7–12 rpm and an angle of repose approximately ⅛ to 5 inches per foot. The furnace has 4 discrete zones with a temperature profile from 200_C. to 1200_C. with either a co-current or a counter current dry air flow at approximately 25–100 SCFM. Another atmosphere that is reducing, for example methane, may be used. The resultant product is an agglomeration of fused microspheres and powder.

The final agglomeration of fused microspheres prepared by this method will have a range of compositions comprising the following:

| | |
|---|---|
| $SiO_2$ | from about 60 to about 75%; |
| $Na_2O$ | from about 10 to about 35%; |
| $K_2O$ | from about 2 to about 20%; |
| $B_2O_3$ | from about 5 to about 20%; and |
| CaO | from about 0.5 to about 12%. |

As used herein, all percentages (%) are percent weight in volume of water prior to heating, also expressed as weight/volume %, % (w/v), w/v, w/v % or simply %, unless otherwise indicated. It should be noted, however, that this example is by no means a limitation of the invention, and that various modifications and improvements in the manufacturing process all fall under the scope of this invention.

It should be noted that the above range of compositions of fused microspheres as disclosed herein, as well as the process of making same, is disclosed in U.S. application Ser. No. 09/302,270, titled Artificial Rock Fragrance Delivery System, filed on Apr. 30, 1999, by Mosbaugh. The present invention incorporates by reference the text and disclosure of application Ser. No. 09/302,270. The range of compositions of fused microspheres as disclosed herein is the subject of U.S. application Ser. No. 09/302,270, which has been allowed but has not yet issued. The process of making fused microspheres as disclosed herein is the subject of a Divisional Application of U.S. application Ser. No. 09/302,270. Said Divisional application, Ser. No.09/779,175, titled Artificial Rock Fragrance Delivery System, by Mosbaugh, was filed on Feb. 8, 2001, under Express Mail Label No. EE469329035US.

The fused agglomeration of microspheres created by Example 1 can be formed into various shapes as desired. The use of room temperature setting binders in the manufacture of aesthetically pleasing shapes from the pre-glass agglomeration adsorptive material is accomplished as described below.

EXAMPLE 2

Forming Shaped Fragrance Delivery Systems

Referring now to FIG. 1, the reader can see that one embodiment of the process of molding the agglomerations of fused microspheres of Example 1 begins by sifting the finished agglomerations of fused microspheres in order to isolate the smallest intact particles and free-flowing powder (1). This is easily accomplished via a sieve or strainer. Various mesh size strainers are commercially available from restaurant supply stores and are well known in the art.

The smallest microsphere particles, along with the free-flowing powder, which pass through the sifting process are then recovered. Those particles which are too large to pass through the sifting apparatus are discarded or used for any other appropriate purpose. In the preferred method, a sifting apparatus is used which allows the user to isolate the free-flowing powder and those particles which are less than two millimeters in size from those particles greater than two millimeters.

Next, it should be decided whether the final shaped fragrance delivery system should have fragrance added (2). If fragrance is to be added, it may be added at this point (3) to the sifted pre-glass particles by vapor deposition, submersion, or any method known in the art. Alternatively, as described in more detail below, fragrance can be added after the shapes are molded. If fragrance is to be added after the shapes are molded, then the sifted particles should be kept dry and away from moisture (4).

As described below, the microsphere particles and free-flowing powder (1) will be mixed with a ceramic binder, resulting in a slurry which may be poured or extruded in order to form certain shapes. Binders were examined according to cost, performance, equipment involved, and ease of use. Two plasters were determined to be very effective, Hydrostone and Hydrocal, both manufactured by U.S. Gypsum. Both are calcined gypsum cements which require minimal heat for setting, do not diminish the adsorption of the pre-glass agglomeration, and provide appropriate visual effects.

When using Hydrostone, for example, the following formulation of constituents should be obtained (5) in order to produce the desired slurry:

Hydrostone gypsum cement binder—7 parts by volume

Mixture of microsphere particles and free-flowing powder (comprised of approximately 60% microsphere particles and 40% free flowing powder)—3.5 parts by volume Water—3 parts by volume In an alternative method, sodium silicate can also be added to form the slurry, resulting in a slurry with a decreased setting time. This is particularly useful when the present invention is to be adapted for use in a large scale manufacturing process.

It should be noted that humidity and ambient conditions, as well as slight variations in the microsphere particles, the free-flowing powder and the Hydrostone material, may call for additional water in order to provide adequate viscosity control of the final slurry. Addition and blending of all the constituents is accomplished in one mixing vessel.

In the preferred method, the adding and mixing of the constituents should occur in the following order: First, the Hydrostone or Hydrocal constituent should be added to the mixing vessel, followed by the water constituent (5). In an alternative method, sodium silicate may be added to the water constituent before the water constituent is added to the mixing vessel. If desired, the fragrance delivery system may be dyed to improve its cosmetic appearance. Colored liquids or dyes can be used, and the resulting pre-glass agglomeration has the color or dye of the liquid absorbed therein. Numerous pigment types may be used. Water-soluble dyes from Pylam Industries may be incorporated into the product via addition with the water, or alternatively via addition with the Hydrostone. Oil-based dyes may be used in this phase, but the addition of a glycol or solvent is also required if oil-based dyes are to be used. In this method, the setting period, as described below, is longer and more Hydrostone must be used for optimum results.

The mixture should then be vigorously mixed (6) by any appropriate means well known to those in the art. Next, the microsphere particles and free-flowing powder constituent should be added to the mixing vessel (7), and the mixture should again be vigorously mixed (8). Finally, additional water may be added as needed to control viscosity (9) such as may be required by the specific molding steps as may be selected according to the present invention.

Next, the slurry is shaped as desired to form the shaped fragrance delivery system (10). For small-scale operations, this may be accomplished by introducing the slurry into a mold of the desired shape (11). In the preferred method, the mold is first treated with a mold release compound well known to those skilled in the art. The preferred molds are vacuum-formed polyethylene that provide for a tight pore stricture for the face in the mold. In an alternative method the slurry can also be poured into pastry icing sacks or other similar devices used to create free form shapes and "extruded" into a variety of shapes (12). The slurry within the mold, or in free form shapes, is then placed under a heat lamp until the contents are dried (13).

Once the molds are dried, the mold is inverted and the molded material slips out. The side of the shaped fragrance delivery system that was adjacent to the mold surface is then allowed to dry. This process typically takes approximately ten minutes.

If fragrance oils or other liquids were not added to the microsphere particles or powder after the sifting step, such fragrance oils or liquids may now be added to the shaped fragrance delivery system. The fragrance oils to be adsorbed by the shaped fragrance delivery system may be modified with various solvents or diluents in order to control the vapor pressure and thus the impact and perception age for the product. Preferred solvents include dipropylene glycol, propylene glycol, SD alcohols, or any other carrier well known to those in the art. Only FDA-approved solvents or diluents should be used for molded shaped fragrance delivery systems which may be used in contact with skin. The fragrance oils may also be dyed to impart color.

Referring now to FIG. 2, one can see that liquids may be added (15) to the dried shaped fragrance delivery systems by either submerging them in liquid (16) or by vapor deposition (17). If the method of submerging is chosen, the dried shapes should first be submerged in the chosen liquid, and the liquid should be mildly agitated while the shapes are allowed to soak. If the method of vapor deposition is chosen, the volatilized fragrance oils are deposited into the shapes via heat and pressure. Regardless of the method chosen, the shapes are then allowed to dry at room temperature or by cold drying (18). After drying, the shaped fragrance delivery systems may be packaged (19).

EXAMPLE 3

Forming Shaped Fragrance Delivery Systems

A small-scale batch of shaped fragrance delivery systems can easily be created after the mixture of fused microsphere particles and free-flowing powder are created according to Example 1. First, measure out each respective constituent.

17 grams Hydrostone 3 grams pre-glass agglomeration blend (comprised of approximately 60%

10 grams water 60 mg of sodium silicate may be added to the water prior to mixing, if desired, for a slurry with a decreased setting time.

Next using a drill with a paint mixing blade mounted above a small mixing bowl, add the constituents and perform the following mixing steps in the following order:

Put Hydrostone in mixing bowl;

Add the water and mix vigorously for 2 minutes;

Add the pre-glass agglomeration, mix vigorously for 2 minutes;

Add back 2 gram aliquots of water for desired viscosity.

The slurry is then poured using a spoon into various half molds that are sprayed with a mold release compound well known to those skilled in the art. The preferred molds are vacuum-formed polyethylene that provide for a tight pore stricture for the face in the mold.

The slurry within the mold is then placed under a heat lamp for approximately 20 minutes depending on the size of the mold or shape. Once the molds are dried, the mold is inverted and the molded material slips out. Subsequent drying of the previously bound face is for approximately 10 minutes. Next, the dried shapes are submerged into the desired fragrance for 3 minutes, removed, and allowed to air dry.

A mass production scheme is very flexible. The addition of the constituents, mixing, and setting of the final slurry may be accomplished by using numerous existing equipment designs well known to those skilled in the art. Concerns are limited to dust control and flammability of fragrance oils.

It is to be understood that the present invention is not limited to the methods described above, but encompasses any and all methods within the scope of the following claims.

I claim:

1. A process for making a shaped fragrance delivery system comprising:
   a. preparing a mixture of adsorptive material comprised of naturally fused microspheres and free-flowing powder, comprising:
      $SiO_2$ about 60 to about 75%;
      $Na_2O$ about 10 to about 35%;
      $K_2O$ about 2 to about 20%;
      $B_2O_3$ about 5 to about 20%; and
      CaO about 0.5 to about 12%;
   b. isolating a portion of said mixture in which all of said naturally fused microspheres and said free-flowing powder are sufficiently small to allow said portion to combine with a binder and water to form a slurry;
   c. combining said portion with a binder and water to form a slurry;
   d. mixing said slurry;
   e. forming said mixed slurry into a desired shape to create a shaped fragrance delivery system; and
   f. drying said shaped fragrance delivery system.

2. A process for making a shaped fragrance delivery system as in claim 1, further comprising:
   a. adding one or more liquids to said shaped fragrance delivery system; and
   b. drying said one or more liquids on said shaped fragrance delivery system.

3. A process for making a shaped fragrance delivery system as in claim 2, wherein said one or more liquids is a fragrance.

4. A process for making a shaped fragrance delivery system as in claim 2, wherein said one or more liquids has aromatic properties.

5. A process for making a shaped fragrance delivery system as in claim 2, wherein said one or more liquids has insect repellant properties.

6. A process for making a shaped fragrance delivery system comprising:
   a. preparing a mixture of adsorptive material comprised of naturally fused microspheres and free-flowing powder, comprising:
      $SiO_2$ about 60 to about 75%;
      $Na_2O$ about 10 to about 35%;
      $K_2O$ about 2 to about 20%;
      $B_2O_3$ about 5 to about 20%; and
      CaO about 0.5 to about 12%;
   b. isolating a portion of said mixture in which all of said naturally fused microspheres and said free-flowing powder are sufficiently small to allow said portion to combine with a binder and water to form a slurry;
   c. adding one or more liquids to said portion;
   d. combining said portion with a binder and water to form a slurry;
   e. mixing said slurry;
   f. forming said mixed slurry into a desired shape to create a shaped fragrance delivery system; and
   g. drying said shaped fragrance delivery system.

7. A process for making a shaped fragrance delivery system as in claim 1, wherein:
   a. said step of combining said portion with a binder and water to form a slurry occurs by combining approximately 7 parts by volume of said binder with approximately 3 parts by volume of said water and approximately 3.5 parts by volume of said portion, wherein said portion is comprised of approximately 40% free-flowing powder and approximately 60% naturally fused microspheres.

8. A process for making a shaped fragrance delivery system as in claim 1, wherein said binder is a calcined gypsum cement.

9. A process for making a shaped fragrance delivery system as in claim 1, further comprising adding sodium silicate to said slurry during said step of combining.

10. A process for making a shaped fragrance delivery system as in claim 1, wherein said step of combining said portion with a binder and water to form a slurry further comprises first adding water-soluble dyes to said water.

11. A process for making a shaped fragrance delivery system as in claim 1, wherein said step of combining said portion with a binder and water to form a slurry further comprises first adding water-soluble dyes to said portion.

12. A process for making a shaped fragrance delivery system as in claim 1, wherein said step of combining said portion with a binder and water to form a slurry further comprises first adding oil-based dyes with a solvent or a glycol to said water.

13. A process for making a shaped fragrance delivery system as in claim 1, wherein said step of combining said portion with a binder and water to form a slurry further comprises first adding oil-based dyes with a solvent or a glycol to said portion.

14. A process for making a shaped fragrance delivery system as in claim 1, wherein said one or more liquids contains dye.

15. A process for making a shaped fragrance delivery system as in claim 1, wherein said step of forming said mixed slurry into a desired shape to create a shaped fragrance delivery system occurs by introducing said slurry into a mold, drying said slurry, and removing said dried slurry from said mold.

16. A process for making a shaped fragrance delivery system as in claim 15, wherein said mold contains a mold release compound prior to said introduction of said slurry.

17. A process for making a shaped fragrance delivery system as in claim 15, wherein said mold is made of polyethylene.

18. A process for making a shaped fragrance delivery system as in claim 1, wherein said step of forming said mixed slurry into a desired shape to create a shaped fragrance delivery system occurs by extruding said slurry in said shape of said shaped fragrance delivery system.

19. A process for making a shaped fragrance delivery system as in claim 15, wherein said step of drying said shaped fragrance delivery system occurs by placing said mold under a heat lamp.

20. A process for making a shaped fragrance delivery system as in claim 2, wherein said step of adding said one or more liquids to said shaped fragrance delivery system occurs by submerging said shaped fragrance delivery system in said one or more liquids.

21. A process for making a shaped fragrance delivery system as in claim 2, wherein said step of adding one or more liquids to said shaped fragrance delivery system occurs by vapor deposition.

22. A process for making a shaped fragrance delivery system as in claim 2, wherein said one or more liquids contains dipropylene glycol, propylene glycol, or SD alcohol.

23. A process for making a shaped fragrance delivery system comprising:
  a. preparing a mixture of adsorptive material comprised of naturally fused microspheres and free-flowing powder comprising an agglomeration of fused microspheres, comprising:
    $SiO_2$ about 60 to about 75%;
    $Na_2O$ about 10 to about 35%;
    $K_2O$ about 2 to about 20%;
    $B_2O_3$ about 5 to about 20%; and
    $CaO$ about 0.5 to about 12%;
  b. sifting said mixture in order to isolate a portion of said mixture in which all of said naturally fused microspheres and said free-flowing powder are less than about two millimeters in size;
  c. combining said portion with a binder and water to form a slurry;
  d. mixing said slurry;
  e. transferring said slurry into a mold;
  f. drying said mold until said slurry substantially dries, creating a shaped fragrance delivery system containing a first side that is in contact with said mold and a second side that is not in contact with a mold;
  g. removing said shaped fragrance delivery system from said mold;
  h. drying said first side of said shaped fragrance delivery system;
  i. adding liquid to said shaped fragrance delivery system; and
  j. drying said shaped fragrance delivery system.

24. A product formed by the process described in claim 1.

* * * * *